United States Patent [19]
Johnson, Jr.

[11] Patent Number: 5,389,065
[45] Date of Patent: Feb. 14, 1995

[54] ANKLE BRACE WITH ATF COMPRESSION

[75] Inventor: Glen W. Johnson, Jr., Summit, N.J.

[73] Assignee: Aircast, Inc., Summit, N.J.

[21] Appl. No.: 77,006

[22] Filed: Jun. 15, 1993

[51] Int. Cl.[6] .............................................. A61F 5/00
[52] U.S. Cl. ..................................... 602/27; 607/108;
607/111; 607/112; 602/13
[58] Field of Search ........................... 602/5, 6, 13, 27;
607/96, 108, 111, 112

[56] References Cited

U.S. PATENT DOCUMENTS

| | | |
|---|---|---|
| 4,280,489 | 7/1981 | Johnson, Jr. . |
| 4,844,094 | 7/1989 | Grim .................................. 602/27 |
| 4,964,402 | 10/1990 | Grim et al. .................... 602/27 X |
| 5,007,416 | 4/1991 | Burns et al. ........................ 602/27 |
| 5,088,478 | 2/1992 | Grim .................................. 602/27 |
| 5,113,877 | 5/1992 | Johnson, Jr. et al. ........... 602/27 X |
| 5,125,400 | 6/1992 | Johnson, Jr. . |

FOREIGN PATENT DOCUMENTS 9306797 4/1993 WIPO ................................. 602/27

OTHER PUBLICATIONS

Wilkerson et al., "Treatment of the Inversion Ankle Sprain: Comparison of Different Modes of Compression and Cryo Therapy", JOSPT, vol. 17, No. 5, May 1993, pp. 240–246.

Wilkerson, "Treatment of the Inversion Ankle Sprain through Synchronous Application of Focal Compression and Cold", Athletic Training, JNATA, vol. 26, Fall 1991, pp. 220–237.

Primary Examiner—Richard J. Apley
Assistant Examiner—Linda C. M. Dvorak

[57] ABSTRACT

A stirrup-type ankle brace having an outer shell member, the shell member having a lateral elongated, substantially rigid, support member with a corresponding supporting cushion thereon substantially coextensive therewith and an opposed medial support member with a corresponding cushion thereon. The lateral supporting cushion has a pre-inflated flap extending the anterior margin of its distal end with enough width to cover the area over and surrounding the anterior talofibular ligament. The flap is compressed against the ATF by a strap of elastic hook-and-loop compatible material. A tab of hook material is attached to the anterior end of the elastic strap so that it can engage the opposite end at any length. The strap is retained between the lateral shell and supporting cushion in the preferred embodiment so as to overlap the flap and compress the ATF ligament and medial malleolus when wrapped around the ankle. It does not wrap around either of the shells, but is at the outside surface of the lateral supporting cushion and the inside surface of the medial supporting cushion in the preferred embodiment.

8 Claims, 2 Drawing Sheets

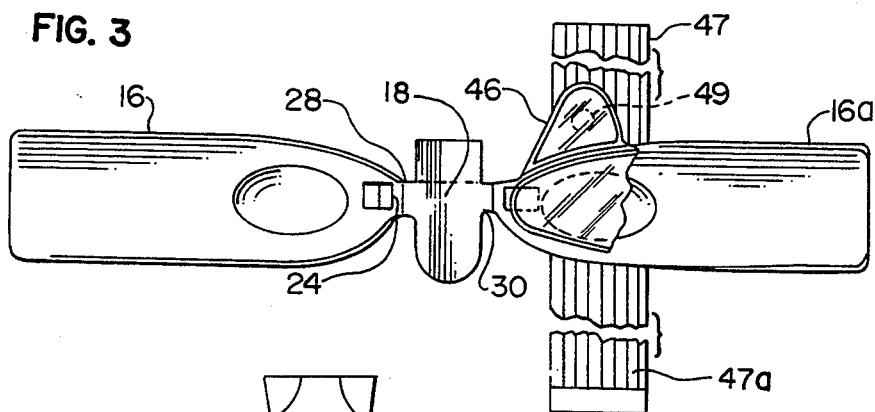
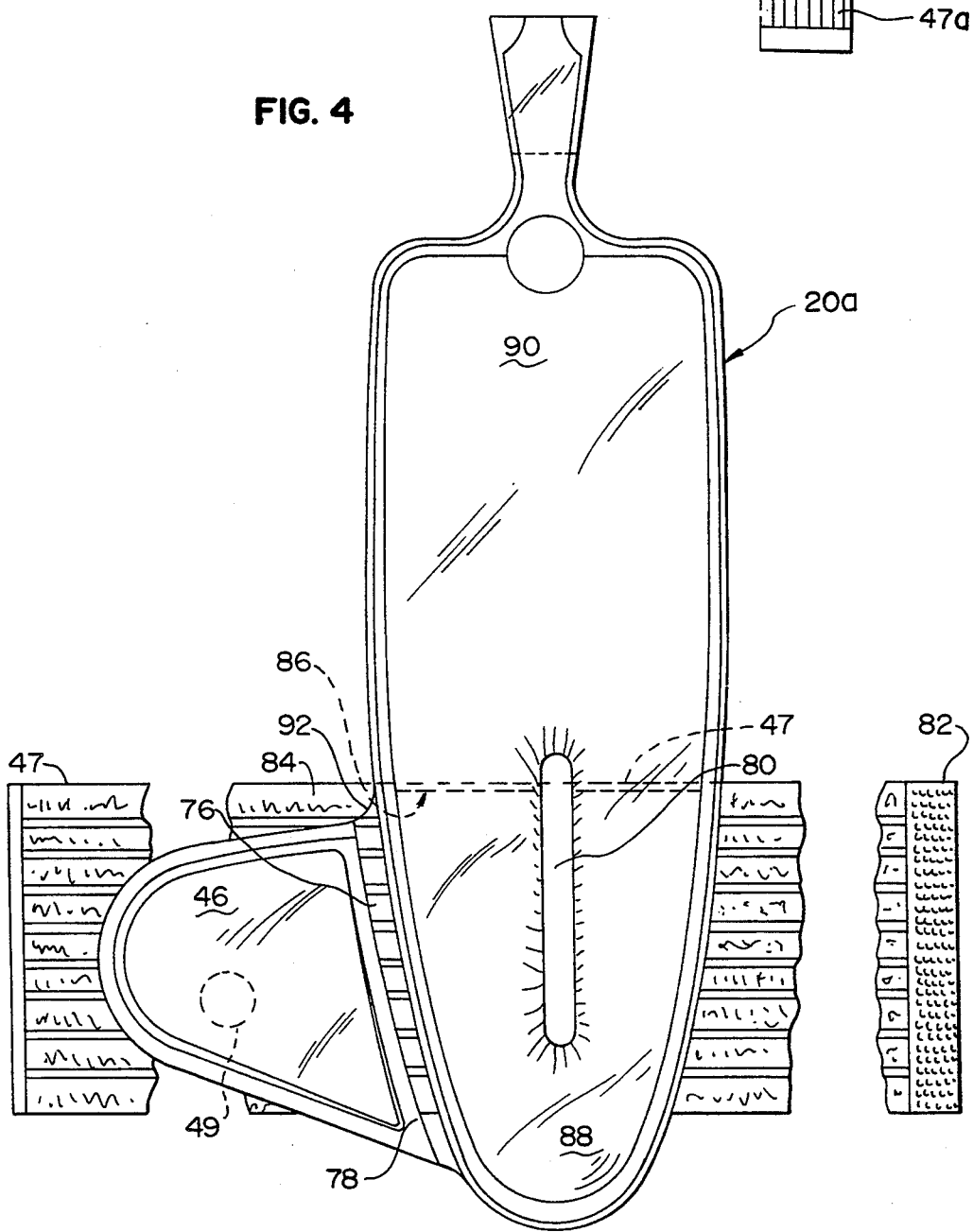

ANKLE BRACE WITH ATF COMPRESSION

FIELD OF THE INVENTION

The present invention relates generally to orthopedic devices and more particularly to ankle braces for stabilizing the ankle against inversion and eversion without limiting normal plantarflexion and dorsiflexion of the ankle while simultaneously providing focal compression of the anterior talofibular ligament (ATFL) from within the ankle brace itself.

BACKGROUND OF THE INVENTION

In the management of certain injuries to the lower extremities such as fractures of the tibia and fibula, malleolar fractures, or severe ankle sprains, it is common to completely immobilize the lower extremity by use of the well-known molded plaster or resin cast.

Once the injured extremity has become stable however, it has been found that recovery may be effected more rapidly by gradually and progressively permitting the extremity to bear weight and undergo other permitted exercises. Thus, for example, an orthopedic brace such as those disclosed in U.S. Pat. Nos. 4,280,489 and 5,125,400, both of which are assigned to the assignee herein and incorporated herein by reference in their entirety, may be utilized. These braces are pneumatic braces featuring one or more rigid outer shell members having associated therewith an inflatable liner or air cell for engaging a body part or limb. Commercial embodiments of the pneumatic brace incorporating the inventions disclosed in these prior patents are adapted to be fixed about the lower leg and typically comprise an outer shell member, or sidewall, in the form of a U-shaped stirrup having inflatable liners or air cells disposed within the stirrup member in co-extensive relation to the upstanding sidewalls thereof. Strap fastening means maintain the member sidewalls in engagement with confronting portions of the lower leg whereby each air cell serves as a firm supporting cushion of pressurized air between the irregular contours of the lower leg and the member sidewalls.

This brace construction is capable of stabilizing the ankle against eversion and inversion while permitting dorsiflexion and plantarflexion and while being worn inside a conventional shoe. Thus ambulatory functionality and permitted exercises are feasible thereby encouraging more rapid recovery from various injuries to the lower extremity, such as ankle sprains, than otherwise would be possible. The braces are used for ankle management in many countries because of their effectiveness, comfort and convenience in mobilizing yet protecting the ankle from re-injury. They have made "functional management" practicable.

The most common ankle injury is a sprain of the anterior talofibular ligament (ATFL) at the anterior margin of the lateral malleolus where swelling and edema originates. Since the ATFL is in the anterior front portion of the ankle, it lies in the uncovered area between the two sides of the stirrup member. To compensate for this uncovered area, many practitioners use a supplemental compression wrap during the initial few days after injury. An elastic ankle wrap is used just for this purpose.

Thus the recovery rate for ankle function following an inversion sprain may be related to the effectiveness of edema control at the injury site. Numerous authors have reported the use of a U-shaped felt or foam rubber device beneath an elastic wrap or adhesive tape for applying focal compression to the soft tissues adjacent to the fibular malleolus. See, for example, Wilkerson et al., "Treatment of the Inversion Ankle Sprain: Comparison of Different Modes of Compression and Cryo Therapy", JOSPT, Volume 17, No. 5, May 1993, pages 240-246. Focal compression consists of pressure application to surface concavities while adjacent proximal convex bony prominences are left uncompressed. See Wilkerson, "Treatment of the Inversion Ankle Sprain through Synchronous Application of Focal Compression and Cold", ATHLETIC TRAINING, JNATA, Volume 26, Fall 1991, pages 220-237. One of the objectives of the studies, as set forth in these articles, was to add focal compression to the uncovered area between the two sides of the stirrup with a pathway up the center of the stirrup for drainage of edema from the area of high pressure to the area of low pressure. Another objective was to add cryotherapy. The study shows that return to function by the patient is indeed faster with both focal compression and cold. But adding the cold temperature to the focal compression produced no better results than applying the focal compression at room temperature. This infers that focal compression accelerates healing but cold does not.

The problem with the prior art devices using a supplemental compression wrap under the stirrup is the inconvenience, bulk, and cost. Further it is an extra element to teach, handle and, maybe, misuse.

SUMMARY OF THE INVENTION

The present invention provides a stirrup-type ankle brace with a focal compression device for the ATFL within the stirrup itself, the device having minimal added complexity, bulk, and cost.

In the present invention, the lateral air cell has a pre-inflated flap or cushioning element extending about 2½ inches from its distal and anterior margin with enough width to cover the area surrounding the ATFL. Ideally, the flap is filled with foam and pre-inflated as a separate compartment so that its air cannot be displaced back into the adjacent distal compartment of the lateral air cell. If the lateral air cell included a separate distal compartment, then the pre-inflated flap could also be in fluid communication with the separate distal compartment such that air could flow into the separate distal compartment. However, a pre-inflated flap in fluid communication with the proximal portion of the lateral air cell would be much less effective because of the displacement of the air from the pre-inflated flap back to the proximal portion of the air cell.

Any type of compressible liner such as foam or gel, neoprene and the like could, of course, be substituted for or used with air cells.

The flap is compressed against the ATFL by a strap of elastic, hook-and-loop compatible material such as SPANDEX. A tab of hook material is attached to the anterior end of the strap so that it can engage its opposite end at any length. This strap is retained between the lateral shell and the air cell so as to overlap the flap and compress the ATFL and the lateral malleolus when wrapped around the ankle. It does not wrap outside either the lateral or the medial shell, the outer rigid shells, but engages the outside surface of the lateral air cell and contacts the inside surface of the medial air cell when the stirrup is in use.

The stirrup is applied by placing the heel of the foot on the heel pad connecting the outer rigid shell members of the stirrup, lifting the lateral shell member to cause the lateral support cushion to contact the ankle, wrapping the elastic strap over the flap and around the ankle and attaching it to itself with the hook and loop, then lifting the medial shell and wrapping the two external wraparound straps conventionally around both the lateral and medial shells to hold them on the leg. Thus the elastic strap and the extra thickness of the extended flap create added compression in the area over and around the ATFL. As is now known, this higher compression of the ATFL will cause the migration of edema to areas of less compression, with eventual dissipation proximately up the leg.

It is important to note that even though the elastic strap wraps around the air cell and ankle and over the flap, it does not constrict circulation as with a conventional circumferential strap. This is because the novel air cell provides several areas of relatively high focal compression along with adjacent channels of low compression that serve as passageways for proximal migration of edema.

Such passageways, of course, exist at the anterior and posterior margins of the flap and distal air cell in the seam formed between the flap and the distal compartment of the lateral air cell. In the preferred embodiment, an additional channel is provided by forming the distal compartment of the lateral air cell into a U-shape with a narrow space formed by the legs of the U. This is accomplished by cutting the foam liner of the distal compartment of the lateral air cell into the shape of a U and the outer and inner layers of plastic film forming the distal compartment are sealed together at the centerline of the U. Thus the arms of the U engage and compress the sides of the lateral malleolus with relatively high focal compression, but the narrow center of the U provides a passageway extending from the higher pressure of the distal portion of the air cell to the lower pressures of the proximal portion of the air cell and beyond.

Thus, the present invention relates to an ankle brace of the type having a shell member, said shell member having a first lateral elongated support member with a first corresponding supporting cushion thereon, and a second opposed medial support member with a second corresponding supporting cushion thereon, each of said support members and supporting cushions having a distal end and a proximal end. The first and second support members are attached together at the distal ends thereof by a flexible web and fastening means adapted to fasten the set of elongated opposed support members about the leg with the supporting cushion placed between the elongated support members, or sidewall members, and the leg and with the flexible web passing under the sole of the foot, the ankle brace further including a cushioning element carried by one of the supporting cushions, said cushioning element having a shape sufficient to cover the area of the anterior talofibular ligament, and means attached to the shell member for engaging the cushioning element to provide focal compression over the area of the anterior talofibular ligament and force edema upwardly from the distal area of the ankle to the proximal area of the ankle.

The invention also relates to a stirrup-type ankle brace comprising first and second spaced apart sidewall portions, each sidewall portion having a substantially rigid outer shell and a flexible support member substantially co-extensive with the outer shell for engaging the ankle portion of the leg on each side thereof, a base portion having side regions attached to the first and second spaced apart sidewall portions such that the spaced apart sidewall portions extend upwardly therefrom, fastening means attached to at least one of the rigid outer shells from maintaining the flexible support members in engagement with corresponding confronting ankle portions, and cushion means carried by at least one of the first and second spaced apart sidewall portions and compressed over at least a portion of the anterior talofibular ligament for providing focal compression thereto.

BRIEF DESCRIPTION OF THE DRAWINGS

These and other objects of the present invention will be more clearly understood when taken in conjunction with the detailed description of the drawings in which like numerals represent like elements and in which:

FIG. 3 is a view in elevation of the preferred embodiment of the air cell for use with the stirrup device, the air cell having formed therewith the extended flap which covers the anterior talofibular ligament and is held in compression thereon by an elastic strap; and FIG. 4 is a plan view of an alternate embodiment of the present invention in which the extended flap, or cushioning element, and the elastic strap are attached to one of the rigid outer shells of the U-shaped stirrup device.

DETAILED DESCRIPTION OF THE DRAWINGS

Figure 1:
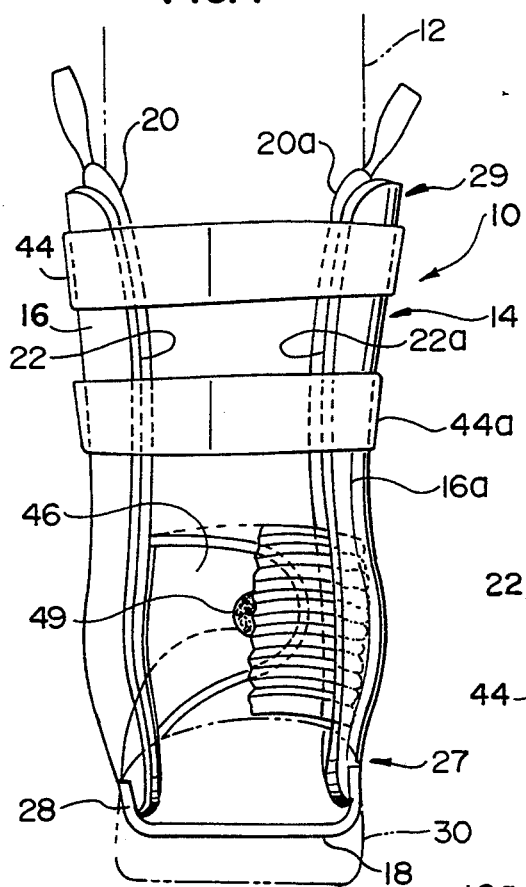
FIG. 1 is a front view in elevation of the stirrup device according to the present invention, depicted in fitted engagement about the lower extremity of a human leg, with a portion of the strap deleted for clarity.

FIG. 1 schematically illustrates a front view of the orthopedic device of the present invention which, in its preferred form, comprises an ankle brace or stirrup device and is generally represented by reference numeral 10. For purposes of illustrating the present invention, the ankle brace 10 is shown in FIG. 1 fitted about the lower extremity of a human limb 12 with the lower extremity being indicated diagrammatically in outline form by broken lines 12. The term "lower extremity" as used herein should be interpreted broadly to include the foot, the ankle, and the lower leg.

Ankle brace 10 comprises a generally U-shaped stirrup member 14 which, in the embodiment shown, has a pair of spaced apart opposed sidewall portions 16, 16a joined to a base portion 18. The base portion 18 may be integrally formed with the opposed sidewall portions 16, 16a or the base portion 18 preferably may be a flexible web having side regions 28, 30 removably and adjustably attached to the first and second spaced apart sidewall portions 16, 16a such that the spaced apart sidewall portions 16, 16a extend upwardly therefrom. A pair of air inflatable flexible liners or air cells 20, 20a are disposed, respectively, on the inwardly facing surfaces 22, 22a of opposed sidewall portions 16, 16a in a generally juxtaposed manner co-extensive therewith. Each sidewall portion 16, 16a extends longitudinally upwardly from base portion 18 and has an arcuate transverse cross-sectional shape sufficient to conform generally to the circumferential contour of the lower leg and ankle as disclosed in U.S. Pat. No. 4,280,489 and U.S. Pat. No. 5,125,400.

The air cells 20, 20a may be of a type as disclosed in either U.S. Pat. No. 4,280,489 or U.S. Pat. No. 5,125,400. The illustrated versions in FIG. 2 include lower pressurizable preinflated chambers 21, 21a interiorly of the air cells 20, 20a which may contain filler members (not shown), of the type as generally shown in FIGS. 11–15 of said '400 patent.

Figure 2:
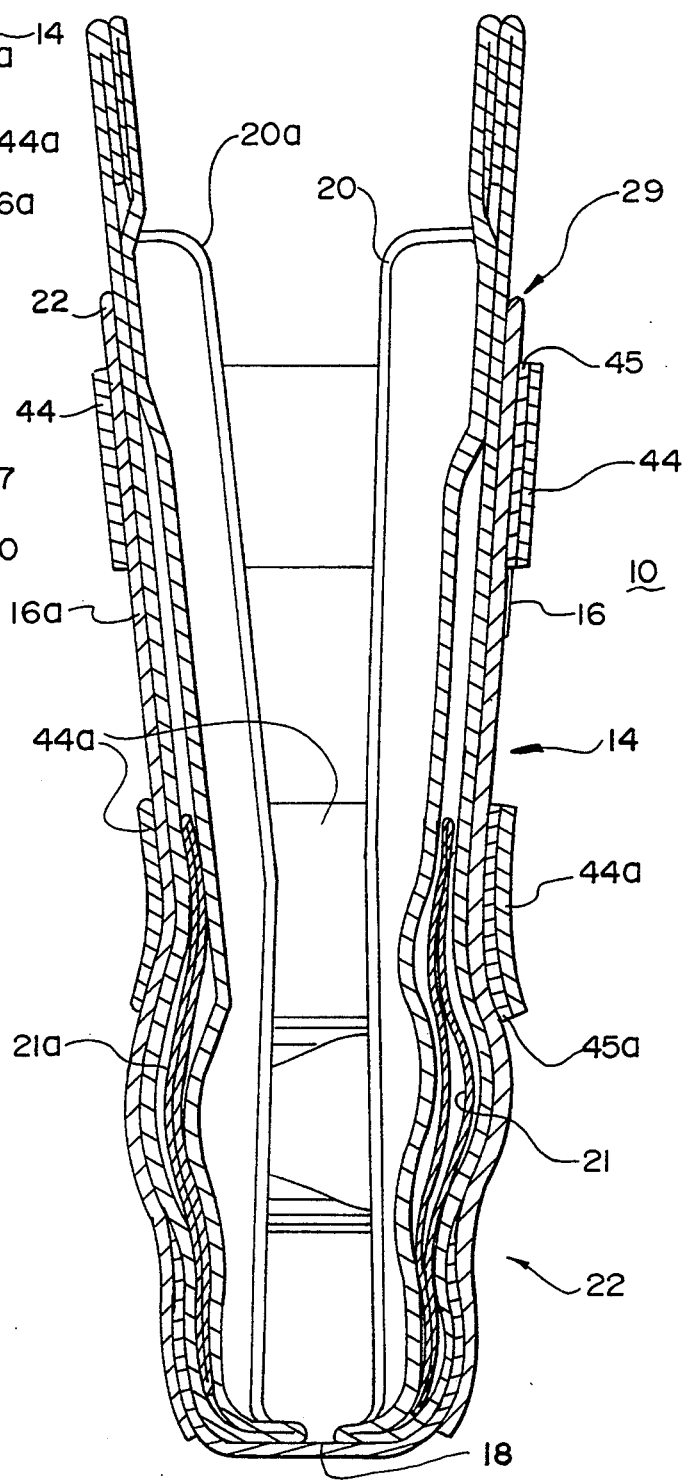
FIG. 2 is an enlarged sectional view of the orthopedic device according to the present invention looking to the from or anterior portion thereof.

Preferably, each air cell 20, 20a is maintained in a position relative to the inside surface 22, 22a of each sidewall portion and relative to the upwardly facing surface of base portion 18 substantially as shown in FIGS. 1 and 2 by means of a double faced adhesive patch, a plurality of such patches, or other suitable fastening means.

In order to maintain the ankle brace 10 in proper fitting engagement about the lower extremity, a pair of longitudinally spaced, circumferentially extending fastener strap members 44, 44a are provided. These fastener straps 44, 44a are preferably pivotally attached at one end to one of said rigid stirrup members, or shells, and have hook-and-loop portions thereon such that the strap can be wrapped circumferentially around the leg and attached to itself. The straps 44, 44a preferably are attached as disclosed in pending U.S. patent application Ser. No. 839,475 filed Feb. 19, 1992 commonly assigned. The straps 44, 44a are intended to engage hook like fasteners indicated schematically at 45, 45a which are integrally molded with the shell 22, as disclosed in commonly assigned copending application Ser. No. 665,343 filed Mar. 6, 1991 and entitled "Method for Injection-Molding an Orthopedic Device and Product of the Method" in which the hook elements are injection molded on the shells as an integral part thereof.

Thus the ankle brace of the type illustrated in FIGS. 1 and 2 has an outer U-shaped shell member, the shell member having a lateral elongated, substantially rigid, support member 16 with a corresponding supporting cushion 20 thereon and an opposed medial, substantially rigid, support member 16a with a corresponding supporting cushion 20a thereon. Each of the support members 16, 16a and supporting cushions 20, 20a have a distal end 27 and a proximal end 29. The support members 16, 16a are attached together at the distal end 27 thereof by a flexible web 18. Fastening means 44, 44a are adapted to fasten the support members 16, 16a about the leg with the supporting cushions 20, 20a placed between the support members 16, 16a and the leg and with the flexible web 18 passing under the sole of the foot.

The novel ankle brace 10 of the present invention also includes, in the preferred embodiment, a cushioning element in the form of a flap 46 (FIG. 3) extending outwardly from the distal and anterior side 78 of the lateral supporting cushion 20a as illustrated in FIG. 3. A circumferential elastic strap 47 passes between the lateral supporting cushion 20a and the inside wall of the lateral substantially rigid support member 16a (see FIG. 1) and has sufficient length such that it extends over the flap 46 and around the leg. Hook and loop fasteners 82 and 84 on the circumferential elastic strap 47 are such that the strap 47 can wrap around the leg over the flap 46 and attach to itself, as shown in partial cut-away view in FIG. 1. It will then provide compression to the flap 46 to cause focal compression to the ATFL and migration of the edema upwardly from the distal high pressure area to the proximal low pressure area.

In addition, at least one spot of "hook" material 49 may be placed on the flap 46 to engage the corresponding "loop" material 84 on the strap 47 such that the strap 47 will tend to pull the flap 46 over the ATFL. Flap 46 is attached to the distal anterior side 78 of the lateral supporting cushion 20a as a pre-inflated compartment in fluid isolation with the lateral supporting cushion 20a. In other words, there is no fluid communication between the interior of flap 46 and the interior of supporting cushion 20a.

A first longitudinally extending low pressure channel 80 is formed in the distal portion 27 of the lateral supporting cushion 20a for proximal migration of edema. As shown in FIG. 3, and as disclosed in detail in U.S. Pat. No. 5,125,400, the distal high pressure portion 88 of the lateral support cushion 20a extends substantially to the upper end of channel 80, shown in phantom lines, and the low pressure area 90 of the lateral support cushion 20a continues upwardly from the boundary 86. Thus the additional channel 80 forms distal compartment 88 into substantially a U-shape with a narrow space formed by the legs of the U and with the upper portion of the U channel 80 extending into the low pressure area 90 of the lateral support cushion 20a. A foam liner, not shown, that is typically present in the supporting cushions 20 and 20a, is cut into a U as shown in FIG. 3 and the outer and inner layers of the plastic film forming the lateral supporting cushions 20 and 20a are sealed together at the centerline of the U. Thus the arms of the U in the distal compartment 88 compress the sides of the lateral malleolus with relatively high focal compression, but the center 80 of the U provides a passageway for edema to the lower pressure area of the proximal compartment 90 and beyond. Thus channel 80 is a first longitudinally extending low pressure channel formed in the distal portion 88 of the lateral supporting cushion 20a for proximal migration of edema. Since the first longitudinally extending low pressure channel 80 extends from the distal high pressure area 88 of the lateral supporting cushion 20a to the proximal low pressure portion 90, the edema can migrate upwardly from the distal high pressure area 88 of the lateral supporting cushion 20a to the proximal low pressure area 90 of the lateral supporting cushion 20a.

A seam 76 is formed by the attachment of the flap 46 to the distal anterior side 78 of the lateral supporting cushion 20a. At this point, the outer and inner layers of the film forming the compartment 88 and the extended flap 46 are sealed together. When the elastic strap 47 is wrapped around the ankle over the extended flap 46, and compression is applied to the flap 46, the seam 76 formed by the attachment of the flap 46 to the distal anterior side 78 of the lateral supporting cushion 20a forms a second longitudinally extending low pressure channel for passageway of edema upwardly from the distal high pressure area 88 to the proximal low pressure area 90.

In another embodiment of the present invention, the lateral supporting cushion 20a may be formed into separate compartments 88 and 90 which do not have fluid communication with each other as suggested by phantom line 86. In such case, the flap 46 may be integrally formed with the high pressure area 88 of the lateral supporting cushion 20a and would be in fluid communication therewith as indicated by the dashed or phantom line 92. In such case, there would be no seam 76 to separate the flap 46 from the high pressure compartment 88 and the interior of flap 46 would be in fluid communication with the interior of the high pressure compartment 88. Thus, in such case, the air cell 20a would have distal portion 88 and proximal inflatable portion 90 forming the lateral elongated support cushion 20a, the distal and proximal portions 88 and 90 being in fluid isolation with each other. The cushioning element or flap 46 would then be formed as an inflatable air cell in fluid communication with only the distal inflatable portion 88 of the lateral support cushion 20a such that compression applied to the cushion of flap element 46 by the compression means or elastic strap 47 would force the edema upwardly.

In another embodiment as shown in FIG. 4, the lateral and medial support members 16 and 16a are again attached to the base portion 18 in any well-known manner. The base portion 18 may have elongated side regions 28 and 30 which extend through slots 24 and 24a to be removably attached to the support members 16 and 16a in any well-known fashion by hooks and loops (not shown). The hooks may be injection molded on the support members 16 and 16a as an integral part thereof as described in commonly assigned copending application Ser. No. 665,343 filed as set forth earlier herein. In this embodiment, the cushioning means, or extended flap 46, is connected with the anterior distal edge of support member 16a and has a first elastic strap 47 also connected with and extending from the anterior distal portion of support 16a while a second elastic strap 47a extends from the distal posterior edge of the support 16a as shown in FIG. 4. Again the elastic straps 47 and 47a are formed with hooks and loops such that they may overlap when wrapped around the ankle and attach to each other, thus holding the cushion means or flap 46 in compression against the ATF ligament. The compression, of course, may be varied by the degree of extension of the flexible straps 47 and 47a.

Thus, there has been disclosed a novel ankle brace that includes ATF ligament compression means within the ankle brace itself. The lateral air cell has a pre-inflated flap extending about 2½ inches from its distal anterior margin with enough width to cover the area surrounding the ATF ligament. Ideally, the flap 46 is filled with foam and pre-inflated as a separate compartment so that its air cannot be displaced back into the adjacent distal compartment 88 of the support cushion or air cell 20a. However, if a separate distal compartment exists in the lateral air cell, then the flap or cushion means could be in fluid communication with the separate distal compartment. The cushion means or flap is compressed against the ATF ligament by a strap of elastic formed with hook-and-loop compatible materials, such as SPANDEX, about 3 inches in width by 12 inches in length. A tab of hook material is attached to the anterior end so that it can engage at the opposite end at any desired length. The strap is preferably retained between the lateral shell and the lateral air cell so as to overlap the flap or cushion means and compress the ATF ligament and medial malleolus when wrapped around the ankle. It does not wrap around either of the shells, but is at the outside surface of the lateral air cell and the inside surface of the medial air cell.

The stirrup is applied by placing the heel on the heel pad, lifting the lateral shell to contact with the ankle, wrapping the elastic strap over the flap and around the ankle to apply compression to the ATF ligament, then lifting the medial shell and attaching the two wrap-around straps conventionally. The elastic strap and the extra thickness of the cushion means or flap create added compression over the ATF ligament and around the ankle. As is well known, this added compression will cause the migration of edema to an area of less compression with eventual dissipation proximally up the leg. It is important to note that even though the elastic strap wraps around the air cell and ankle, it does not constrict circulation as would a conventional circumferential strap. This is because the novel air cell provides several areas of relatively high focal compression along with adjacent channels of low compression that serve as passageways for proximal migration of edema. Such passageways exist at the anterior and posterior margins of the flap and distal air cell and the seam between the flap and distal compartment. An additional channel is provided by forming the distal compartment of the lateral air cell into a U-shape. The arms of the U compress the sides of the lateral malleolus with relatively high focal compression but the center of the U provides a passageway for the edema to the lower pressures of the proximal compartment and beyond.

It should be noted that although lateral sprains of the ATF ligament are most common, medial sprains of the deltoid ligaments cause similar swelling toward the anterior margin of the stirrups medial support. For these injuries, the flap, the strap, and the U-shaped distal compartment can, of course, all be relocated to the medial side of the stirrup.

While the invention has been shown and described with respect to a particular embodiment thereof, this is for the purpose of illustration rather than limitation and other variations and modifications of this embodiment herein shown and described will be apparent to those skilled in the art all within the intended spirit and scope of the invention. Accordingly, the patent is not to be limited in scope and effect to the specific embodiment is shown and described nor in any other way that is inconsistent with the extent to which the progress and the art has been advanced by the invention.

What is claimed is:

1. An ankle brace having a shell member, said shell member having a lateral elongated support member with a corresponding supporting cushion thereon and an opposed medial support member with a corresponding supporting cushion thereon, each of said supporting members and supporting cushions having a distal end and a proximal end, said support members being attached together at the distal ends thereof by a flexible web and having fastening means adapted to fasten the set of elongated support members about the leg with the supporting cushion placed between the elongated support member and the leg, and with the flexible web passing under the sole of the foot, the ankle brace further including:

a cushioning element carried by one of the supporting cushions and comprising a flap extending outwardly from the distal anterior side of the lateral supporting cushion, said cushioning element having a shape sufficient to cover the area of the anterior talofibular ligaments;

a circumferential elastic strap passing between the lateral supporting cushion and the lateral support member and having sufficient length such that it extends over said cushioning element; and hook-and-loop fasteners on said circumferential elastic strap such that said strap can attach to itself and provide compression to the flap to cause focal compression over the area of the anterior talofibular ligament and migration of the edemia upwardly from the distal area of the ankle to the proximal area of the ankle.

2. The ankle brace of claim 1 wherein the flap is attached to the distal anterior side of the lateral supporting cushion as a pre-inflated compartment in fluid isolation with the lateral supporting cushion.

3. The ankle brace of claim 2 further comprising a first longitudinally extending low pressure channel formed in the distal portion of the lateral supporting cushion for proximal migration of edema.

4. The ankle brace of claim 3 further comprising:
a low pressure area in the proximal portion of the lateral supporting cushion;
an area of higher pressure in the distal portion of the lateral supporting cushion; and
said first longitudinally extending low pressure channel extending from the distal high pressure area of the lateral supporting cushion to the proximal low pressure portion such that edema can migrate upwardly in the low pressure channel from the distal high pressure area of the lateral supporting cushion to the proximal low pressure of the lateral supporting cushion.

5. The ankle brace of claim 4 further comprising a seam formed by the attachment of the flap to the distal anterior side of the lateral support cushion, said seam forming a second longitudinally extending low pressure channel for passage of edema upwardly from the distal high pressure area to the proximal low pressure area.

6. The ankle brace of claim 1 further comprising:
a distal and a separate proximal inflatable air cell forming said lateral elongated support cushion, said distal and proximal air cells being in fluid isolation with each other; and
the cushioning element being formed as an inflatable air cell in fluid communication with only the distal inflatable air cell such that compression applied to the cushioning element by said compression means forces edema upwardly.

7. An ankle brace comprising:
first and second spaced apart sidewall portions, each sidewall portion having a substantially rigid outer shell and a flexible support member substantially co-extensive with the outer shell for engaging the distal portion of the leg on each side thereof;
a base portion having side regions attached to the first and second spaced apart sidewall portions such that the spaced apart sidewall portions extend upwardly therefrom;
fastening means attached to at least one of the rigid outer shells for maintaining said flexible support member in engagement with corresponding confronting ankle portions;
a flap extending from one of the flexible support members over the area of the anterior talofibular ligament; and
a flexible strap passing between said one of the flexible support members and its corresponding substantially rigid outer shell and having a length sufficient to pass over said flap and apply a selectively variable pressure thereto.

8. The ankle brace as in claim 7 further including hook members on the flap and corresponding loop members on said flexible strap such that the strap can be stretched to apply a desired compression to the flap and then held in place by engagement of the hook members and corresponding loop members.

* * * * *